(12) United States Patent
Washburn et al.

(10) Patent No.: US 7,364,854 B2
(45) Date of Patent: Apr. 29, 2008

(54) NUCLEOTIDE MIXTURE FOR IMPROVED NUCLEIC ACID AMPLIFICATION PERFORMANCE

(75) Inventors: Brian Washburn, Durham, NC (US); Douglas Lovern, Durham, NC (US); Hwa-Tang Thomas Wang, Encinitas, CA (US); Lawrence Burg, Framingham, MA (US)

(73) Assignee: bioMerieux, Inc, Durham, NC (US)

( * ) Notice: Subject to any disclaimer, the term of this patent is extended or adjusted under 35 U.S.C. 154(b) by 9 days.

(21) Appl. No.: 11/040,371

(22) Filed: Jan. 21, 2005

(65) Prior Publication Data

US 2006/0019266 A1 Jan. 26, 2006

Related U.S. Application Data

(60) Provisional application No. 60/538,816, filed on Jan. 23, 2004, provisional application No. 60/538,815, filed on Jan. 23, 2004, provisional application No. 60/538,814, filed on Jan. 23, 2004.

(51) Int. Cl.
*C12Q 1/68* (2006.01)
*C12P 19/34* (2006.01)

(52) U.S. Cl. .................. 435/6; 435/91.1; 435/91.2

(58) Field of Classification Search ............. None
See application file for complete search history.

(56) References Cited

U.S. PATENT DOCUMENTS

| | | | |
|---|---|---|---|
| 5,399,491 A | 3/1995 | Kacian et al. | |
| 5,405,950 A | 4/1995 | Mock et al. | |
| 5,411,876 A * | 5/1995 | Bloch et al. | 435/91.2 |
| 5,633,364 A | 5/1997 | Mock et al. | |
| 6,271,004 B1 | 8/2001 | Warthoe | |
| 6,312,928 B1 | 11/2001 | Van Gemen et al. | |
| 2001/0041334 A1* | 11/2001 | Rashtchian et al. | 435/6 |
| 2002/0119534 A1* | 8/2002 | Ihlenfeldt et al. | 435/91.1 |

FOREIGN PATENT DOCUMENTS

| | | |
|---|---|---|
| DE | 19612779 | 10/1997 |
| EP | 1026261 | 8/2000 |
| WO | WO98/44161 | 10/1998 |
| WO | WO03/054209 | 7/2003 |

OTHER PUBLICATIONS

Green ("General PCR Protocol" http://www.biology.lsa.umich.edu/research/labs/maddock/protocols/PCR/general_pcr_protocol.html. Feb. 17, 1996).*
International Search Report, European Patent Office, in International Application No. PCT/US2005/002414 (form PCT/ISA/210) (date of mailing: Feb. 6, 2006).
Eds. Ausubel et al., "*A Compendium of Methods from Current Protocols in Molecular Biology*" Short Protocols in Molecular Biology, $2^{nd}$ edition., Chapter 15, pp. 15.1-15.27, John Wiley & Sons, New York (1991).

* cited by examiner

*Primary Examiner*—Kenneth R. Horlick
*Assistant Examiner*—Christopher M. Babic
(74) *Attorney, Agent, or Firm*—Elizabeth S. Worley (57) ABSTRACT

The present invention relates to modification of amplification buffer used in amplification reactions. The modifications result in a significant improvement in results of amplification In particular, the present invention provides methods and buffers for performing an amplification reaction utilizing a buffer comprising nucleotide triphosphates comprising treating the buffer to substitute a portion of the nucleotide triphosphates with nucleotide diphosphates.

16 Claims, 7 Drawing Sheets

| 37°C LAR | | RATE A | | | RESULTS SUMMARY | | |
|---|---|---|---|---|---|---|---|
| Log | RNA/mL | Rep 1 | Rep 2 | Rep 3 | Mean | STDEV | % CV |
| 0.0 | 0 | 0.08 | 0.14 | 0.01 | 0.08 | 0.06 | 82.5 |
| 1.0 | 10 | 0.41 | 0.12 | 0.02 | 0.18 | 0.20 | 111.6 |
| 1.5 | 32 | 0.39 | 0.46 | 0.93 | 0.59 | 0.29 | 49.5 |
| 2.0 | 100 | 1.87 | 2.31 | 3.39 | 2.52 | 0.78 | 31.0 |
| 2.5 | 316 | 5.69 | 10.46 | 4.99 | 7.05 | 2.98 | 42.3 |
| 3.0 | 1000 | 29.59 | 18.53 | 10.05 | 19.39 | 9.80 | 50.5 |
| 3.5 | 3162 | 47.40 | 50.42 | 49.52 | 49.11 | 1.55 | 3.2 |
| 4.0 | 10000 | 150.79 | 203.71 | 122.50 | 159.00 | 41.22 | 25.9 |
| 4.5 | 31620 | 317.60 | 461.05 | 81.46* | 389.32 | 101.44 | 26.1 |
| 5.0 | 100000 | 606.88 | 580.99 | 503.90 | 563.92 | 53.57 | 9.5 |
| 5.5 | 316200 | 570.86 | 703.38 | 737.66 | 670.64 | 88.09 | 13.1 |
| 6.0 | 1000000 | 658.34 | 384.99 | 1,348.71 | 797.35 | 496.67 | 62.3 |

| 37°C LAR | | RATE B | | | RESULTS SUMMARY | | |
|---|---|---|---|---|---|---|---|
| Log | RNA/mL | Rep 1 | Rep 2 | Rep 3 | MEAN | STDEV | % CV |
| 0.0 | 0 | 0.06 | 0.18 | 0.07 | 0.10 | 0.07 | 67.1 |
| 1.0 | 10 | 14.18* | 1.79 | 0.08 | 0.94 | 1.21 | 128.9 |
| 1.5 | 32 | 8.75 | 14.72 | 45.70 | 23.06 | 19.83 | 86.0 |
| 2.0 | 100 | 67.18 | 88.77 | 229.91* | 77.97 | 15.27 | 19.6 |
| 2.5 | 316 | 319.11 | 471.16 | 273.36 | 354.54 | 103.55 | 29.2 |
| 3.0 | 1000 | 1,446.79 | 967.54 | 587.08 | 1000.47 | 430.80 | 43.1 |
| 3.5 | 3162 | 2,421.57 | 1,984.31 | 2,276.47 | 2227.45 | 222.71 | 10.0 |
| 4.0 | 10000 | >4200.00 | >4200.00 | >4200.00 | #DIV/0! | #DIV/0! | #DIV/0! |
| 4.5 | 31620 | >4200.00 | >4200.00 | >4200.00 | #DIV/0! | #DIV/0! | #DIV/0! |
| 5.0 | 100000 | >4200.00 | 2,367.65 | >4200.00 | 2367.65 | #DIV/0! | #DIV/0! |
| 5.5 | 316200 | 1,756.86 | 2,001.96 | 2,186.27 | 1981.70 | 215.42 | 10.9 |
| 6.0 | 1000000 | 1,017.99 | 851.43 | 2,791.18 | 1553.53 | 1075.06 | 69.2 |

| 4°C LAR | | RATE A | | | RESULTS SUMMARY | | |
|---|---|---|---|---|---|---|---|
| Log | RNA/mL | Rep 1 | Rep 2 | Rep 3 | MEAN | STDEV | % CV |
| 2.0 | 100 | 0.39 | 0.45 | NA | 0.42 | 0.05 | 10.9 |
| 2.5 | 316 | 1.25 | 1.62 | NA | 1.44 | 0.26 | 18.1 |
| 3.0 | 1000 | 3.62 | 3.79 | NA | 3.70 | 0.12 | 3.3 |
| 3.0 | 1000 | 3.63 | 3.33 | 1.35 | 2.77 | 1.24 | 44.9 |

| 4°C LAR | | RATE B | | | RESULTS SUMMARY | | |
|---|---|---|---|---|---|---|---|
| Log | RNA/mL | Rep 1 | Rep 2 | Rep 3 | MEAN | STDEV | % CV |
| 2.0 | 100 | 8.47 | 13.29 | NA | 10.88 | 3.41 | 31.3 |
| 2.5 | 316 | 38.42 | 41.13 | NA | 39.78 | 1.92 | 4.8 |
| 3.0 | 1000 | 100.67 | 98.88 | NA | 99.78 | 1.27 | 1.3 |
| 3.0 | 1000 | 93.95 | 102.57 | 115.81 | 104.11 | 11.01 | 10.6 |

FIG. 7

```
                              SEQUENCE LISTING

<160> NUMBER OF SEQ ID NOS: 6

<210> SEQ ID NO 1
<211> LENGTH: 17
<212> TYPE: DNA
<213> ORGANISM: Hepatitis C virus
<220> FEATURE:
<221> NAME/KEY: misc_feature
<222> LOCATION: (1)..(17)
<223> OTHER INFORMATION: 1259

<400> SEQUENCE: 1
ccctagtcac ggctagc                                                    17

<210> SEQ ID NO 2
<211> LENGTH: 23
<212> TYPE: DNA
<213> ORGANISM: Hepatitis C virus
<220> FEATURE:
<221> NAME/KEY: misc_feature
<222> LOCATION: (1)..(23)
<223> OTHER INFORMATION: 1236

<400> SEQUENCE: 2
aggccagtaa cggcactctc tgc                                             23

<210> SEQ ID NO 3
<211> LENGTH: 14
<212> TYPE: DNA
<213> ORGANISM: Hepatitis C virus
<220> FEATURE:
<221> NAME/KEY: misc_feature
<222> LOCATION: (1)..(14)
<223> OTHER INFORMATION: 1246

<400> SEQUENCE: 3
ctgtgaaagg tccg                                                       14

<210> SEQ ID NO 4
<211> LENGTH: 16
<212> TYPE: DNA
<213> ORGANISM: Hepatitis C virus
<220> FEATURE:
<221> NAME/KEY: misc_feature
<222> LOCATION: (1)..(16)
<223> OTHER INFORMATION: 1247

<400> SEQUENCE: 4
tgagccgcat gactgc                                                     16

<210> SEQ ID NO 5
<211> LENGTH: 98
<212> TYPE: RNA
<213> ORGANISM: Hepatitis C Virus Type I
<220> FEATURE:
<221> NAME/KEY: 3'UTR
<222> LOCATION: (1)..(98)

<400> SEQUENCE: 5
gguggcucca ucuuagcccu agucacggcu agcugugaaa gguccgugag ccgcaugacu      60
gcagagagug cugauacugg ccucucugca gaucaugu                             98
```

```
<210> SEQ ID NO 6
<211> LENGTH: 98
<212> TYPE: RNA
<213> ORGANISM: Hepatitis C Virus Type II
<220> FEATURE:
<221> NAME/KEY: 3'UTR
<222> LOCATION: (1)..(98)
<220> FEATURE:
<221> NAME/KEY: variation
<222> LOCATION: (72)..(72)
<223> OTHER INFORMATION: Sequence variation from Hepatitis C virus Type
      I
<220> FEATURE:
<221> NAME/KEY: variation
<222> LOCATION: (74)..(75)
<223> OTHER INFORMATION: Sequence variation from Hepatitis C virus Type
      I
<220> FEATURE:
<221> NAME/KEY: variation
<222> LOCATION: (81)..(81)
<223> OTHER INFORMATION: Sequence variation from Hepatitis C virus Type
      I

<400> SEQUENCE: 6
gguggcucca ucuuagcccu agucacggcu agcugugaaa gguccgugag ccgcaugacu      60
gcagagagug ccguaacugg ucucucugca gaucaugu                              98
```

NUCLEOTIDE MIXTURE FOR IMPROVED NUCLEIC ACID AMPLIFICATION PERFORMANCE

CROSS-REFERENCE TO RELATED APPLICATIONS

This application claims the benefit of U.S. Provisional Patent Application No. 60/538,815 filed on Jan. 23, 2004, U.S. Provisional Patent Application No. 60/538,814 filed on Jan. 23, 2004, and U.S. Provisional Patent Application No. 60/538,816 filed on Jan. 23, 2004.

FIELD OF THE INVENTION

The present invention relates to methods of increasing the product yield of nucleic acid amplification reactions, with the method particularly useful for diagnostic assays. The present invention particularly relates to buffers useful in nucleic acid amplification reactions.

BACKGROUND OF THE INVENTION

Nucleic acid amplification has proven useful in numerous clinical applications including the detection and/or diagnosis of infectious diseases and pathological genomic abnormalities as well as nucleic acid polymorphisms that may not be associated with any pathological state. Nucleic acid amplification is particularly useful in circumstances where the quantity of the targeted nucleic acid is relatively small compared to other nucleic acids present in a sample, where only a small amount of the targeted nucleic acid is available, where the detection technique has low sensitivity, or where more rapid detection is desirable. For example, infectious agents may be accurately identified by detection of specific characteristic nucleic acid sequences. Because a relatively small number of pathogenic organisms may be present in a sample, the DNA extracted from these organisms typically constitutes only a very small fraction of the total DNA in the sample. Specific amplification of the characteristic DNA sequences, if present, greatly enhances the sensitivity and specificity of the detection and discrimination processes.

Generally, the currently known amplification schemes can be broadly grouped into two classes based on whether the enzymatic amplification reactions are driven by continuous cycling of the temperature between the denaturation temperature, the primer annealing temperature, and the amplicon (product of enzymatic amplification of nucleic acid) synthesis temperature, or whether the temperature is kept constant throughout the enzymatic amplification process (isothermal amplification). Typical cycling nucleic acid amplification technologies (thermocycling) are polymerase chain reaction (PCR), and ligase chain reaction (LCR). Specific protocols for such reactions are discussed in, for example, Short Protocols in Molecular Biology, 2.sup.nd Edition, A Compendium of Methods from Current Protocols in Molecular Biology, (Eds. Ausubel et al., John Wiley & Sons, New York, 1992) chapter 15. Reactions which are isothermal include: transcription-mediated amplification (TMA), nucleic acid sequence-based amplification (NASBA), and strand displacement amplification (SDA).

U.S. Pat. No. 4,683,195 (Mullis); U.S. Pat. No. 4,965,188 (Mullis); and U.S. Pat. No. 4,683,202 (Mullis) describe a polymerase chain reaction (PCR) utilizes DNA polymerase, complementary primer molecules and repeated cycles of thermal reactions to exponentially replicate target nucleic acid molecules. Isothermal target amplification methods include transcription-based amplification methods, in which an RNA polymerase promoter sequence is incorporated into primer extension products at an early stage of the amplification (WO 89/01050), and further target sequence, or target complementary sequence, is amplified by transcription steps and digestion of an RNA strand in a DNA/RNA hybrid intermediate product. See, for example, U.S. Pat. Nos. 5,169,766 and 4,786,600. These methods include transcription mediated amplification (TMA), self-sustained sequence replication (3SR), Nucleic Acid Sequence Based Amplification (NASBA), and variations there of. See, for example, Guatelli et al. Proc. Natl. Acad. Sci. U.S.A. 87:1874-1878 (1990); U.S. Pat. Nos. 5,766,849 5,399,491; 5,480,784; 5,766,849; and 5,654,142 (TMA); and U.S. Pat. No. 5,130,238 (Malek et al.); U.S. Pat. No. 5,409,818 (Davey et al.); U.S. Pat. No. 5,654,142 (Kievits); and U.S. Pat. No. 6,312,928 (Van Gemen et al.) (nucleic acid sequence-based amplification (NASBA) techniques). U.S. Pat. No. 5,792,607 (Backman) describes amplification methods referred to as ligase chain reactions (LCR). U.S. Pat. No 5,744,311 (Fraiser); U.S. Pat. No. 5,648,211 (Fraiser) and U.S. Pat. No. 5,631,147 (Lohman), describe isothermal amplification systems based on strand displacement amplification (SDA). Other approaches include Q.beta. replicase, strand displacement assay (SDA), transcription mediated iso CR cycling probe technology, nucleic acid sequence-based amplification (NASBA) and cascade rolling circle amplification (CRCA). Additional U.S. Patent documents which describe nucleic acid amplification include U.S. Pat. Nos. 4,876,187; 5,030,557; 5,399,491; 5,485,184; 5,554,517; 5,437,990; 5,399,491 and 5,554,516.

While many advances have been made in the area of amplification of nucleic acids, there is still a need to improve the product yield, to achieve improved sensitivity and thus to provide more useful assays. The present invention provides methods and buffers that provide increased amplification performance of a selected nucleic acid.

SUMMARY OF THE INVENTION

The present invention provides a method for performing an amplification reaction utilizing a buffer comprising nucleotide triphosphates comprising treating the buffer to substitute a portion of the nucleotide triphosphates with nucleotide diphosphates.

The present invention additionally provides an amplification reaction utilizing a buffer comprising nucleotide triphosphates comprising treating the buffer, prior to adding enzyme and template to the buffer, by heating the buffer to a selected temperature for a selected period of time, the temperature and time each sufficient to increase the ratio of nucleotide diphosphates to nucleotide triphosphates in the buffer.

The present invention further provides a buffer for amplification of nucleic acids with nucleotide triphosphates, comprising nucleotide triphosphates and nucleotide diphosphates, wherein at least one nucleotide diphosphate is present in a ratio of from 10:90 to 80:20 total nucleotide diphosphate:total nucleotide triphosphate.

Further, the present invention provides a buffer for amplification of nucleic acids with nucleotide triphosphates, comprising nucleotide triphosphates and nucleotide diphosphates, wherein at least one nucleotide diphosphate is present in a ratio of from 35:65 to 80:20 total nucleotide diphosphate:total nucleotide triphosphate.

BRIEF DESCRIPTION OF THE DRAWINGS

FIG. 4 is a table providing the results (3 sets "Reps") of HIV nucleic acid amplification using LAR buffer subjected to incubation at either 4° C. or 37° C., each for 69 days. * indicates a spiked control different from the standard dilution. "CV" is coefficient of variance.

FIG. 7.

DETAILED DESCRIPTION OF THE INVENTION

The present invention relates to modification of the amplification buffer for amplification reactions. The modifications result in a significant improvement in results of amplification As stated above, the present invention provides a method for performing an amplification reaction utilizing a buffer comprising nucleotide triphosphates comprising treating the buffer to substitute a portion of the nucleotide triphosphates with nucleotide diphosphates. The present invention further provides a buffer comprising nucleotide triphosphates wherein the buffer has been treated in a manner that results in the substitution of a portion of the nucleotide triphosphates with nucleotide diphosphates.

As used in the specification and the claims, to "substitute" includes any means by which a portion of the nucleotide triphosphates (NTPs) are replaced by nucleotide diphosphates (NDPs), including, for example any chemical, physical or mechanical means by which this may be accomplished. For example, a portion of the NTPs may simply be left out of the buffer and that portion replaced by NDPs, or a portion of the NTPs may be converted to NDPs, such as by heating the buffer as described herein. The portion replaced should be a portion wherein amplification is improved, e.g., wherein the level of amplification is increased or the time of amplification necessary to have a useful result is reduced or assay sensitivity is increased.

As used in the claims, "treatment" can include any means by which the substitution of a portion of the nucleotide triphosphates with nucleotide diphosphates can be accomplished without significant detrimental effects to the end-point use of the treated buffer, e.g., without significantly decreasing the resulting amplification. For example, the substitution of a portion of the nucleotide triphosphates with nucleotide diphosphates can be accomplished by heat-treating the buffer, as described herein. Alternatively, another example of achieving such substitution is by replacing, in the amplification buffer, a portion of the initial amount of NTPs with NDPs, maintaining the original concentration of nucleotides (all NTPS and NDPs) in the reaction. That is, a portion of the original standard amount NTPs are left out of the reaction and that same portion is replaced by NDPs in the reaction. This example is also further described herein.

In a preferred embodiment, the treatment comprises, prior to adding enzyme and template to the buffer, heating the buffer to a selected temperature for a selected period of time, the temperature and time each sufficient to increase the ratio of nucleotide diphosphates to nucleotide triphosphates in the buffer. "Heating" as used in the claims means heating the buffer to a temperature above ambient, or room, temperature. Heating can mean placing the buffer in an appropriate heating apparatus set for the selected temperature, but ideally it includes bringing the buffer temperature to that selected temperature. Heating temperatures can range from just above room temperature to the boiling point of the buffer, with preferable temperatures falling within that range. For example, a preferred temperature range is between about 25° C. and about 75° C., more preferably between about 25° C. and about 65° C., more preferably between about 37° C. and about 65° C. When describing a temperature, in the claims, "about" typically means within two, and preferably one, degree of the stated temperature. The time period for heating can be selected based upon the temperature selected. In general, the higher the temperature selected, the shorter the preferred period of time, and the lower the temperature, the longer the preferred period of time; i.e., the temperature and the time selected for that temperature are typically inversely related. For example, if a selected temperature is between about 37° C. and about 55° C., the time period may preferably be at least about 7 days; if a selected temperature is above about 55° C., the time period may preferably be up to about 4 days.

As taught herein, improvements to amplification buffers can be achieved by heating a selected amplification buffer at a selected temperature for a selected period of time. Typically, the period of time, regardless of the temperature selected, will be at least about 12 hours, more preferably 18 hours, and even more preferably, 24 hours. Furthermore, particularly at lower temperatures (e.g., 37° C. or lower), the period of time can be significantly longer. For example, the period of time can be at least about 14 days; it can be at least about 21 days; it can be at least about 30 days; it can be at least about 45 days; and it can be at least about 69 days. Given the teachings provided herein, the skilled artisan can select a temperature and incubation time optimal for a particular amplification reaction. In particular, a skilled artisan, given the teachings herein, can select a desired ratio of NDPs to NTPs and determine the optimal temperature and incubation time for the buffer to achieve the desired ratio of NDPs to NTPs.

As used in the claims to "increase the ratio" means to increase the ratio to a point wherein amplification is improved, e.g., wherein the level of amplification is increased, the time of amplification necessary to have a useful result is reduced, or assay sensitivity is increased. As used in the claims "the ratio of at least one nucleotide diphosphate to total nucleotide triphosphate" is the ratio of NDPs to NTPs, regardless of whether the NDPs contributing to the buffer include one, two, three or all four NDPs (i.e., ADP, CDP, GDP and/or TDP), and regardless of what mixture of NDPs comprise the portion of NDPs. The NDPs can be any selected combination of one, two, three or four NDPs, at any selected ratios of one NDP to any other. Based upon the teachings provided herein, the skilled artisan can select specific combinations of NDPs suitable for the particular amplification reaction to be performed. Furthermore, as taught herein, heating can be used to achieve the desired ratio of NDPs to NTPs without necessarily the need particularly to measure which and what portion of NDPs are present in the buffer. One can readily determine the relative proportions of NDPs and NTPs in any prepared buffer of the invention after treating by heat, at a selected temperature and for selected time period, using means such as those described herein, e.g., HPLC analysis.

A preferred embodiment is one wherein the selected temperature and time period are sufficient to increase the ratio of at least one nucleotide diphosphate to total nucleotide triphosphate to a range from about 5:90 to about 80:20 total nucleotide diphosphate:total nucleotide triphosphate. More preferred is a ratio of a range of from about 10:90 to about 80:20 total nucleotide diphosphate:total nucleotide triphosphate. Yet more preferred is a ratio of a range from about 35:65 to about 80:20 total nucleotide diphosphate: total nucleotide triphosphate. As used to describe a ratio within the invention, "about" can provide for slight variations outside the recited numerical range wherein the herein demonstrated improved function of the buffer is retained. Preferred buffers of the invention have a ratio of total nucleotide diphosphate:total nucleotide triphosphate of 35:65, 40:60; 45:55, 50:50, 55:45, 60:40, 65:35, 70:30, 75:35, and 80:20. As mentioned above, the total nucleotide diphosphate can comprise any selected combinations of nucleotides, including modified nucleotides.

As taught herein, improvements to amplification buffers can comprise treating the buffer wherein such treatment comprises replacing a portion of at least one nucleotide triphosphate in the buffer with nucleotide diphosphate. In a preferred embodiment, the portion of nucleotide triphosphates replaced with nucleotide diphosphates is selected from between about 5% and 80%. As used herein "about X%" can provide for slight variations outside the stated numerical percentage wherein the buffer retains improved functioning taught herein. Specifically preferred buffers have replaced at least 10% of the NTPs with NDPs, and more preferred buffers have replaced 10%, 15%, 20%, 25%, 30%, 35%, 40%, 45%, 50%, 55%, 60%, 65%, 70%, 75% and 80% of the NTPs with NDPs. A more preferred range is between about 10% and 80%, 15% and 80%, 15% and 70%, 20% and 65%, 30% and 65%, 35% and 60%, and 35% and 50%.

The present invention additionally includes buffers for amplification of nucleic acids. Such buffers can be made, for example, by the methods described herein. The invention particularly provides a buffer for amplification of nucleic acids with nucleotide triphosphates, comprising nucleotide triphosphates and nucleotide diphosphates, wherein the buffer has been treated in a manner that results in the substitution of a portion of the nucleotide triphosphates with nucleotide diphosphates. A manner that results in the substitution of a portion of the nucleotide triphosphates with nucleotide diphosphates can include any means by which a portion of the nucleotide triphosphates (NTPs) are replaced by nucleotide diphosphates, such as described herein. For example, a portion of the NTPs may simply be left out of the buffer and that portion replaced by NDPs, or a portion of the NTPs may be converted to NDPs, such as by heating the buffer as described herein.

In particular, the invention provides a buffer for amplification of nucleic acids with nucleotide triphosphates, comprising nucleotide triphosphates and nucleotide diphosphates, wherein at least one nucleotide diphosphate is present in a ratio of from 10:90 to 80:20 total nucleotide diphosphate:total nucleotide triphosphate. More preferred is a ratio of a range of from about 10:90 to about 80:20 total nucleotide diphosphate:total nucleotide triphosphate. Yet more preferred is a ratio of a range from about 35:65 to about 80:20 total nucleotide diphosphate:total nucleotide triphosphate. Preferred buffers of the invention have a ratio of total nucleotide diphosphate:total nucleotide triphosphate of 35:65, 40:60; 45:55, 50:50, 55:45, 60:40, 65:35, 70:30, 75:35, and 80:20. As mentioned above, the total nucleotide diphosphate can comprise any selected combinations of nucleotides, including modified nucleotides.

A buffer for amplification of nucleic acids with nucleotide triphosphates, comprising nucleotide triphosphates and nucleotide diphosphates, wherein the buffer has been treated in a manner that results in the substitution of a portion of the nucleotide triphosphates with nucleotide diphosphates.

In the methods and buffers of the present invention, amplification enzymes typically would be added after the heating step, to avoid inactivating the enzymes, though this may not be necessary for use of thermostable enzymes. The buffers of the present invention can be stored under standard conditions, e.g., 4° C., with standard shelf life. The buffer can further comprise selected ingredients for the assay to be performed. Standard amplification buffer formulations are well known in the art, and they can be adapted readily for any of the present inventive buffers, following the teachings herein. For example, buffers can include Tris, magnesium and salt. Buffers can further comprise DMSO. Buffers can further comprise glycerol. More specifically, buffers can include Tween, such as Tween 80, Tris, EDTA, KCl, ZnAc, MgCl, glycerol, DMSO, Na Azide, primers, and/or probes.

Additionally provided herein is a buffer for amplification of nucleic acids comprising greater than 5% Tween 80. Buffers are provided herein that are useful for many amplification reactions, wherein the buffer comprises greater than 5% Tween 80, more preferably greater than 8% Tween 80, greater than 10% Tween 80. A preferred buffer can have 12.5% Tween 80. A buffer can have up to 15% Tween 80. Such buffers can be particularly useful for isothermal amplification reactions. Additionally, they can be preferable when the target of amplification has high secondary structure. Known buffers (e.g., for TMA, U.S. Pat. No. 5,399,491) can be modified to increase the amount of Tween 80 in accordance with the teachings of this invention to create buffers of this invention. Such buffers can further comprise other ingredients; for example the buffer can further comprise DMSO; the buffer can further comprise glycerol; the buffer can further comprise salt. More specifically, such buffers can additionally include Tris, EDTA, KCl, ZnAc, MgCl, glycerol, DMSO, Na Azide, primers, and/or probes. A particularly preferred buffer of the present invention would have both (1) Tween 80 present at greater than 5% and (2)

substitution of a portion of the nucleotide triphosphates with nucleotide diphosphates; however, each of these characteristics provides an improvement in amplification.

Buffers typically contain all four nucleotides, adenine, guanine, thymidine and cytosine; however, for certain applications, it may be that fewer than all four bases are desired. Furthermore, in general, modified nucleotides can be used in addition to the standard nucleotides or in partial or full substitution thereof. Such modified oligonucleotides are known in the art; some examples include hydroxymethyl nucleotides, methylated nucleotides, fluorinated nucleotides, alpha this phosphate nucleotides, amine-modified nucleotides, methoxy nucleotides, carboxymethyl nucleotides, thiol nucleotides, inosine, dihydrouridine, psuedouridine, wybutosine, queuosine, C7dGTP. Additional modified nucleotides are found in U.S. Pat. Nos. 5,405,950 and 5,633,364 (both, Mock and Lovern).

The present invention further provides a kit comprising a buffer of the invention. Such kits can include, in addition to the buffer, one or more additional component, such as instructions for use of the buffer, reaction containers, and additional reagents such as amplification enzyme(s), primers, probes, additional NTPs and/or NTPs, sterilized water, lysis buffer, stop buffer, and the like.

Amplification methods are well known to those of skill in the art, and such artisans can readily apply the teachings provided herein to a selected amplification method. The amplification can be performed utilizing any amplification method that utilizes NTPs, such as DNA polymerase-based amplification reaction or a transcription-based amplification reaction. Amplification can be performed, for example, by thermocycling methods or isothermal methods. The present methods and buffers are particularly useful, and preferably used in, transcription based amplification methods, for example, NASBA and TMA. Transcription based amplification methods often utilize single stranded RNA as the input material, although single or double stranded DNA can likewise be used as input material. When a transcription based amplification method is practiced on a sample with single stranded RNA (of the "plus" sense) with additional sequences on both the 3'-end and the 5' end of the target sequence, a pair of oligonucleotides that is conveniently used with the methods can include (1) a first oligonucleotide (often referred to as a "promoter-oligonucleotide", or "P1" primer) that is capable of hybridizing to the 3-end of the target sequence, which oligonucleotide has the sequence of a promoter (preferably the T7 promoter) attached to its 5' end (the hybridizing part of this oligonucleotide has the opposite polarity as the plus RNA used as input material); and (2) a second oligonucleotide ("primer") which comprises the 3' end of the target sequence (this oligonucleotide has the same polarity as the plus RNA). The present methods and buffers can also be utilized for PCR, RT-PCR, SDA and other amplification reactions known to those of skill in the art.

The nucleic acid target to be amplified can be any selected target susceptible to amplification, including RNA and DNA targets. Many such targets are known to the skilled artisan, and they can include human, animal, viral, bacterial, parasitic and other nucleic acids. Target nucleic acids can preferably include the nucleic acids of infectious agents, and particularly regions of the genomes or gene products of such infectious agents that are useful for detecting and/or specifically identifying the agent. For example, one can amplify a region of Hepatitis C virus (HCV) or Human Immunodeficiency virus (HIV). Examples of such infectious agents include bacteria such as *salmonella*, *shigella*, *chlamydia*, and *neisseria*, viruses such as hepatitis viruses, adenoviruses, human papilloma viruses, enteroviruses, and parasites such as plasmodium. In addition, the target nucleic acid can be genetic sequences indicative of genetic disorders such as sickle cell anemia, .alpha.-thalassemia, .beta.-thalassemia, and cystic fibrosis. Target nucleic acid can also be genes associated with disease states such as insulin-dependent diabetes or certain cancers, or nucleic acids in HLA typing. The skilled artisan can readily adapt the present methods and buffers to a selected nucleic acid target, given the teachings herein.

EXAMPLES

The present invention describes experiments and observations related to modification of amplification buffer which resulted in a significant increase in assay sensitivity. Two different methods were used; 1) heating of the TMA amplification buffer (RAR) at 37° C., 55° C., 65° C., or 2) replacing a portion of the nucleotide triphosphates in the amplification buffer with nucleotide diphosphates. The heating method was shown to result in conversion of nucleotide triphosphates to nucleotide diphosphates, and thus both methods likely improve sensitivity by the same mechanism.

Example 1

HCV Assay Materials and Methods

To evaluate the effects of the buffer modifications on amplification, RAR buffer and standard VIDAS Probe D2 qHCV assay conditions as described below were used, except for modifications of the RAR buffer as noted. Target nucleic acid was Hepatitis C virus (HCV) (3' Non-translated region: Type I, SEQ ID NO: 5; Type II: SEQ ID NO:6). Briefly, in vitro transcript containing HCV (~1 KB total) was incubated with basematrix and lysis buffer to prepare the sample. HCV target and internal control RNA were then captured to paramagnetic particles with an oligonucleotide complementary to the 3' end of HCV (primers and probes are listed in Table 1). Captured RNA was washed and then resuspended in RAR buffer (see modifications described below), which contained all of the reagents needed for amplification except enzymes and target (see Table 2). The RAR-resuspended purified target was then added to VIDAS Probe strips (containing all additional reagents required for TMA amplification and detection, such as enzymes, probes, wash solutions, and detection substrate). TMA amplification was carried out in bioMerieux prototype AmpStations (5 min. 60° C. denaturation; 70 min. 42° C. amplification), and then transferred to VIDAS instruments, which carried out sequence-specific capture of the amplicons, washing, and detection with alkaline phosphatase-conjugate probe specific for the 3' end and fluorescent "MUP" substrate. Three sets of data were obtained from VIDAS:

1) HCV detection A (Diluted sample with low SA substrate, for high titers)
2) HCV detection B (Undiluted sample with high SA substrate, for low titers)
3) IC detection (low IC="invalid assay").

Results are typically provided as numerical "Part A" Rates for highly fluorescent samples, or "Part B" Rates for low fluorescence samples.

TABLE 1

HCV Primer and Probe sequences

```
1259 (primer P2) (nt 17-33)
CCCTAGTCACGGCTAGC                              (SEQ ID NO: 1)

1236 (primer P1 (promoter-primer) (nt 83-61)
AGGCCAGTAACGGCACTCTCTGC-T7 promoter            (SEQ ID NO: 2)

1246 (AKP probe) (nt 32-46)
CTGTGAAAGGTCCG                                 (SEQ ID NO: 3)
(methoxynucleotides; alkaline phosphatase label)

1247 (SPR probe) (nt 47-62)
TGAGCCGCATGACTGC                               (SEQ ID NO: 4)
(methoxynucleotides; AMVE)
```

"Nt" references the position, within the 1-98 sequences of the 3' Non-Translated Region (HTR) of HCV, the primer/probe binds.

TABLE 2

RAR Buffer Formulation

| | |
|---|---|
| Tween 80 | 12.5% |
| Tris pH 7.9 | 95 mM |
| EDTA | 0.375 MM |
| KCl | 50 MM |
| ZnAc | 0.0765 MM |
| MgCl | 20.75 MM |
| Glycerol | 10% |
| DMSO | 5% |
| ATP | 4 MM |
| CTP | 3 MM |
| GTP | 6 MM |
| UTP | 2 MM |
| d-ATPs | 1 MM |
| d-CTPs | 1 MM |
| d-GTPs | 1 MM |
| d-TTPs | 1 MM |
| Na Azide | 0.06% |
| P1 Primer | 40 NM |

Example 2

RAR Buffer Heating Results

This process consists of application of heat to RAR (also known as 1:1 LAR:PRB16 mix, or 1× LAR:PRB), resulting in increased performance. Several key sets of data describe the invention, as follows.

Figure 1:
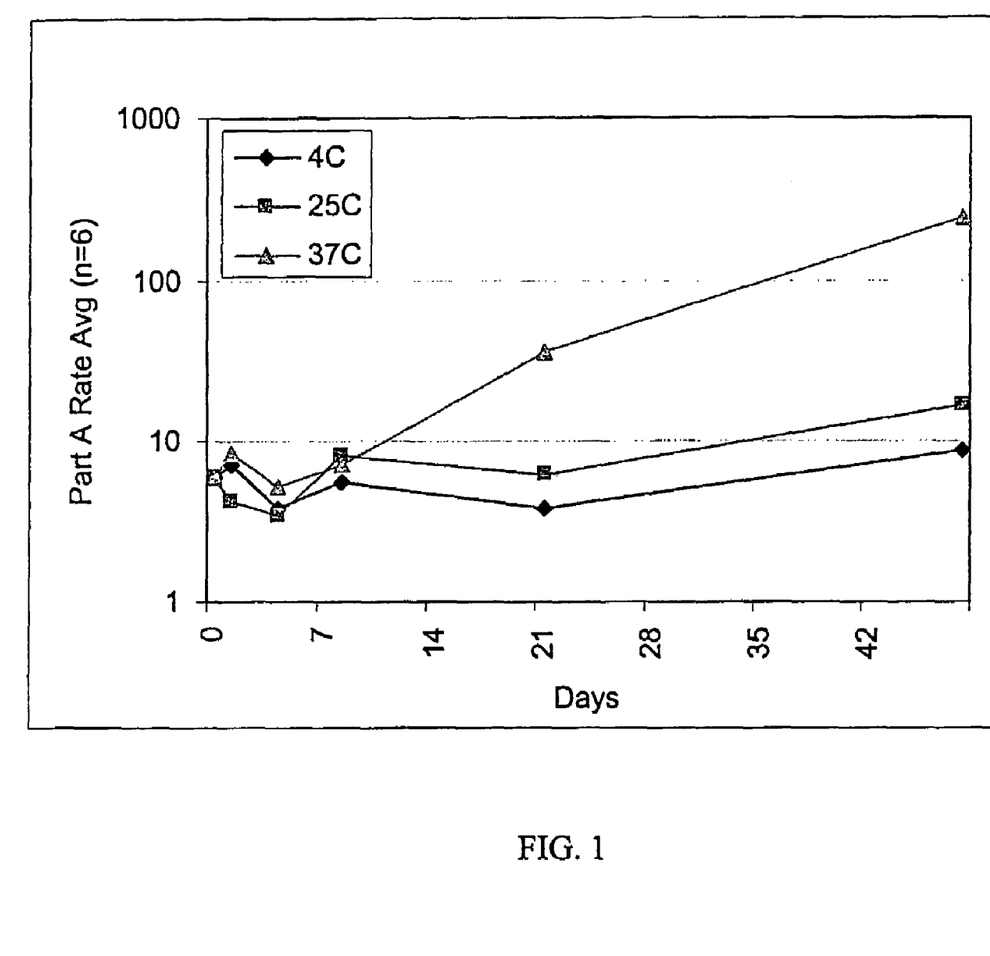
FIG. 1 provides the results of HCV amplification with RAR buffer subjected to extended incubation at 4° C. (--◇--), 25° C. (--□--), and 37° C. (--Δ--), for time lengths (days) indicated, up to 48 days. Part A Rate is measured in fluorescence units.

During the course of accelerated stability testing, it was observed that extended incubation of HCV RAR buffer at 37° C. results in a significant increase in detected amplification product (see FIG. 1). The increase continues up to 48 days of incubation (final timepoint), resulting in a 41-fold increase in performance.

Figure 2:
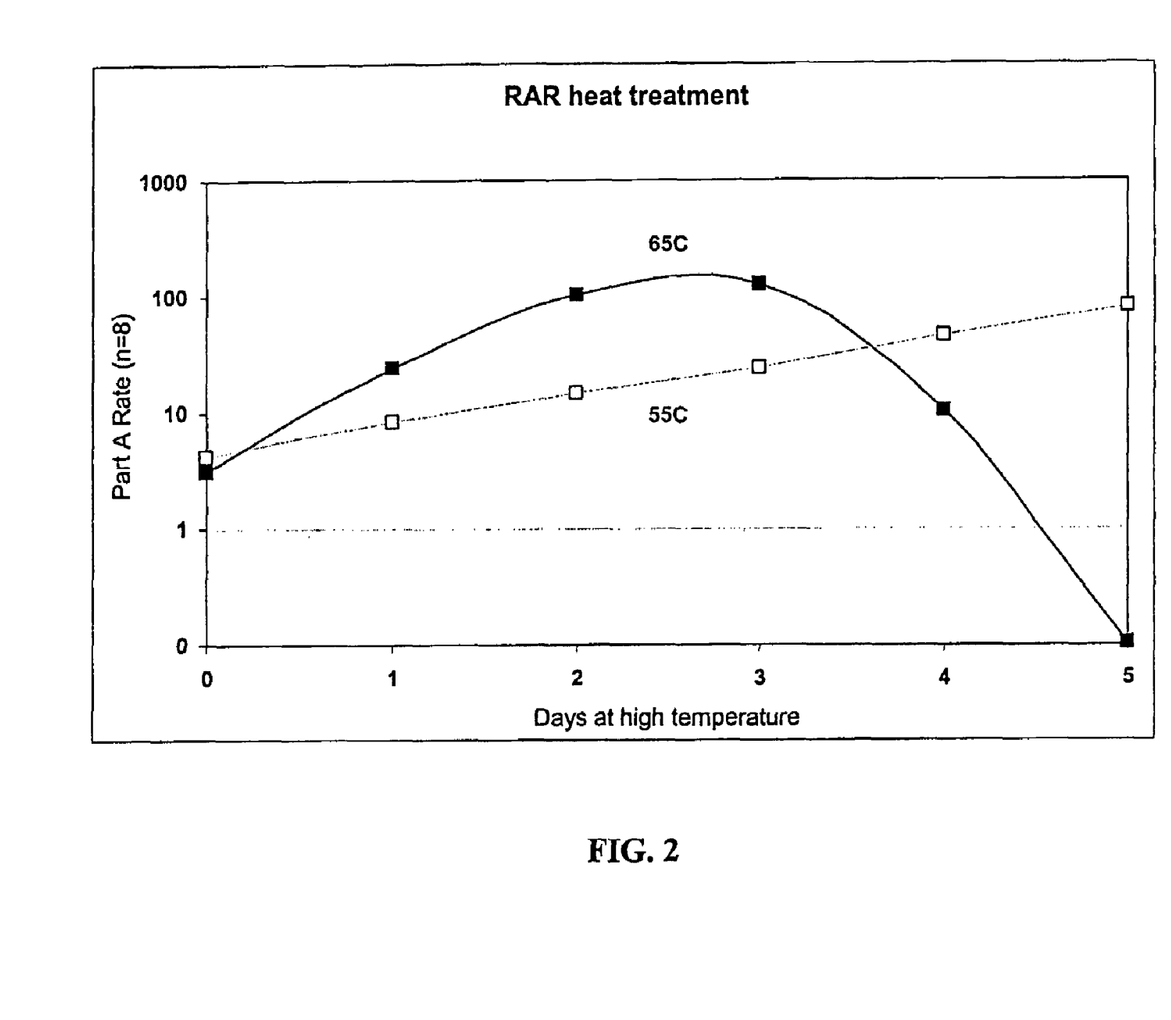
FIG. 2 shows the results of HCV nucleic acid amplification with RAR buffer subjected to extended incubation at 55° C. & 65° C., for the time lengths indicated, up to 5 days, showing rapid increase in rates (relative to lower temperatures of incubation) of improved amplification performance results.

Additional experiments demonstrated that this alteration occurs even faster at higher temperatures (see Table 3 and FIG. 2). Incubation at 65° C. resulted in a ~40-fold increase in HCV detection within 2-3 days. 65° C. incubation beyond 3 days resulted in decreased performance, whereas 55° C. incubation up to 5 days (final timepoint) gave continued increases. It is presumed (but not known) that the decreased performance beyond 3 days at 65° C. is due to excessive degradation of critical assay components (perhaps nucleotide triphosphates).

TABLE 3

| | Days | | | | | |
|---|---|---|---|---|---|---|
| | 0 | 1 | 2 | 3 | 4 | 5 |
| Part A 65 C. | 3.10 | 23.65 | 103.96 | 128.23 | 10.05 | 0.10 |
| STD | 1.85 | 16.64 | 60.56 | 56.04 | 4.10 | 0.07 |
| % CV | 60% | 70% | 58% | 44% | 41% | 68% |
| Part A 55 C. | 4.25 | 8.26 | 14.75 | 23.48 | 44.96 | 79.99 |
| STD | 3.29 | 3.19 | 3.44 | 7.03 | 37.44 | 41.97 |
| % CV | 77% | 39% | 23% | 30% | 83% | 52% |

Figure 3:
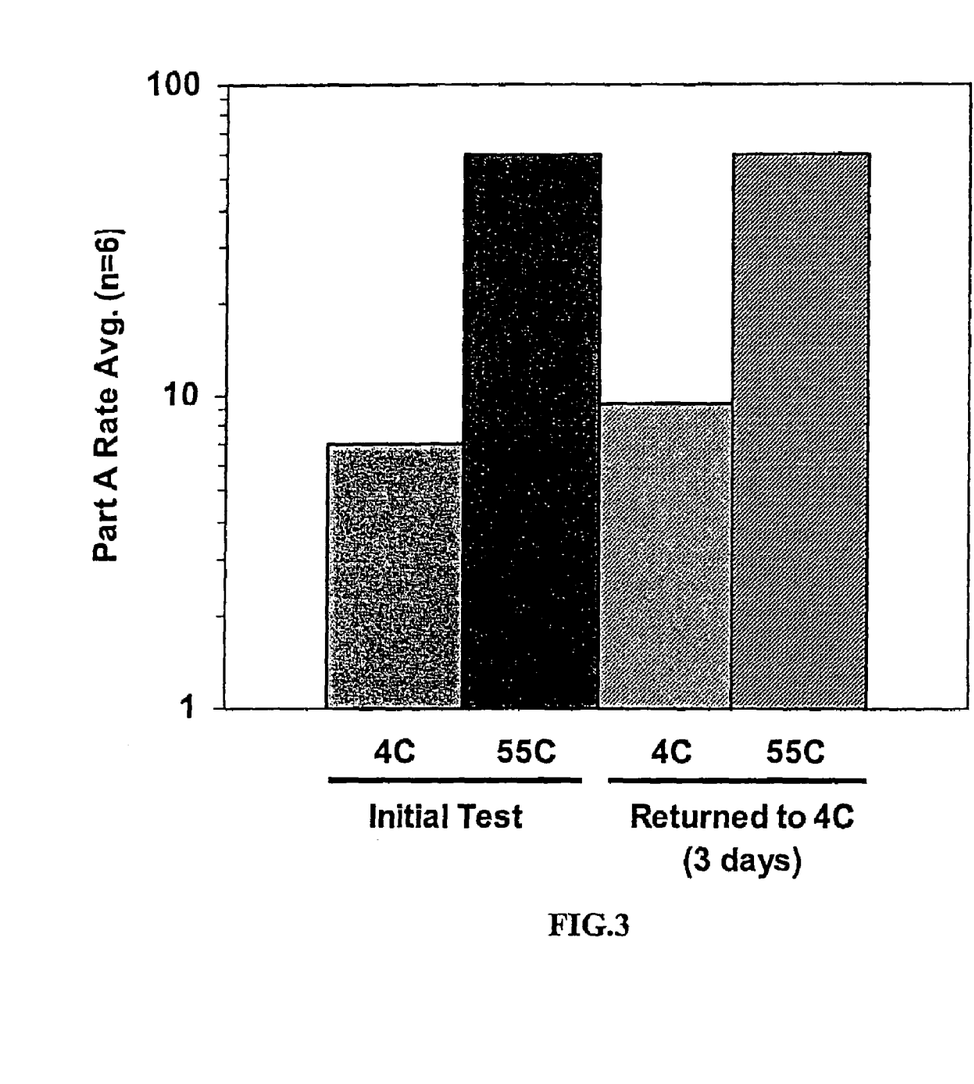
FIG. 3 provides HCV nucleic acid amplification results with RAR buffer heated to 55° C., then returned to 4° C. for 3 days, showing that the treated buffer fully maintained the higher amplification performance after return to 4° C.

The temperature-induced modification creates a stable alteration. 55° C.-preheated amplification reaction buffer returned to 4° C. for 3 days (longest point tested) fully maintained the higher amplification performance (see FIG. 3).

Example 3

HIV Assays

A beneficial effect of heat treatment (37° C.) was also noted for HIV amplification. For these experiments Liquid Amplification Reagent ("LAR") buffer was used. The nucleotide sequences used in the HIV assay differed in that the target, primer and probe sequences had no significant similarity to HCV (except for the T7 promoter tail on the P1 primer), and the composition of HIV LAR and HCV RAR are different in many respects (such as that LAR uses HEPES instead of Tris and Triton instead of Tween, has no KCl or DMSO, and has significantly higher (about 2-fold) concentrations of nucleotides and Mg, and a lower pH (7.4 instead of 7.9). HIV formulation and method of use are as follows:

HIV LAR [46 mM HEPES, 41.1 mM $MgCl_2$, 0.153 mM ZnAc, 0.25 mM EDTA, 10.25% (v/v) glycerol, 5% (v/v) Triton-X-100, 0.095% (w/v) $NaN_3$, pH 7.4, 6.0 mM each rNTP, 2.4 mM each dNTP, 50 nM T7 TMA primer, 150 nM non-T7 TMA primer] was mixed with an equal volume of SRB [46 mM HEPES, 40 mM KCl, 0.15 mM ZnAc, 0.25 mM EDTA, 10.25% glycerol, 0.095% $NaN_3$, pH7.4] to create the final amplification reagent (analogous to RAR).

Figure 5:
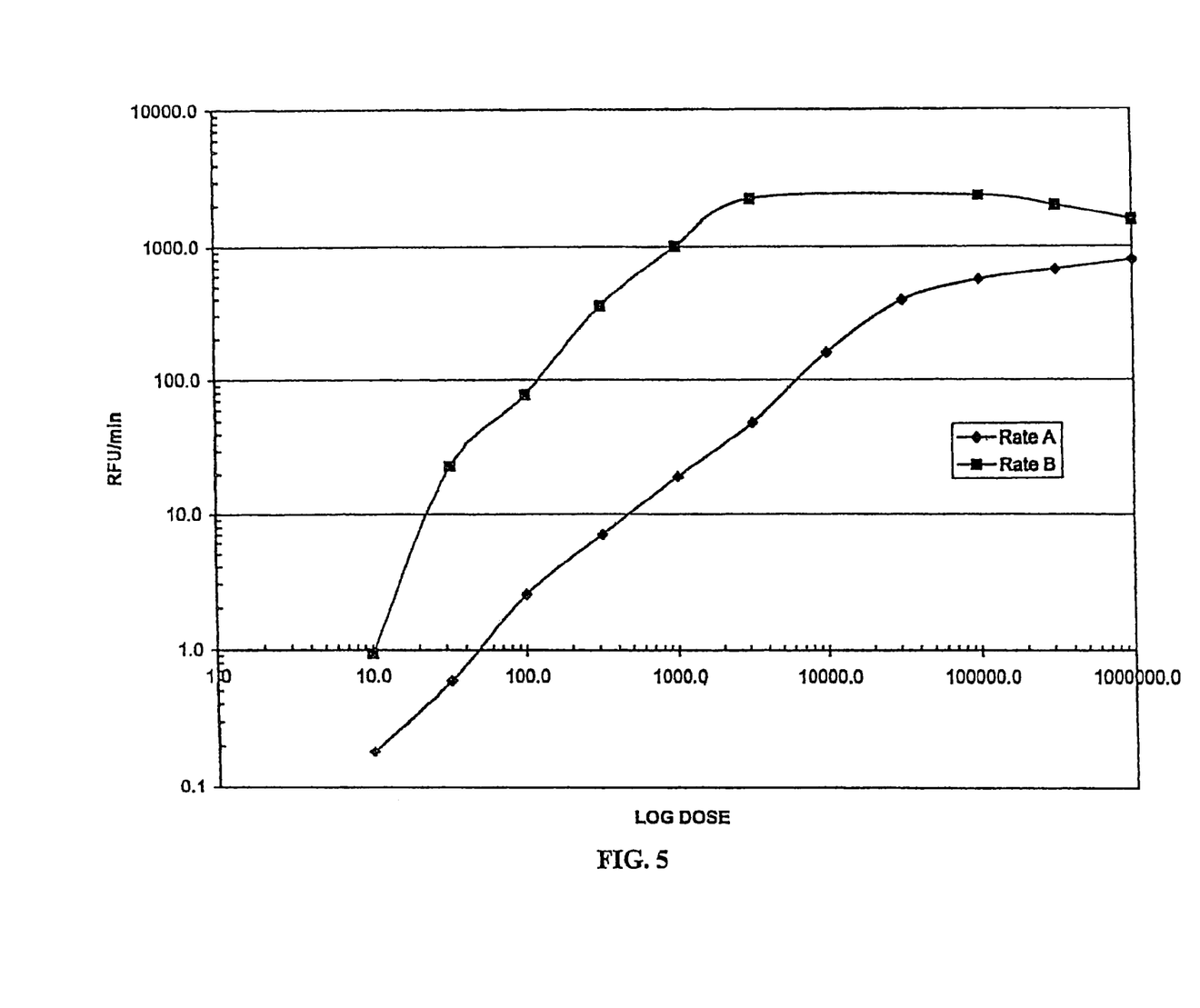
FIG. 5 provides a graph of the dynamic range for Rates A (--◆--) and B (--■--) (see FIG. 4) using LAR buffer stored at 37° C. for 69 days. "RFU" is relative fluorescence unit.
Figure 6:
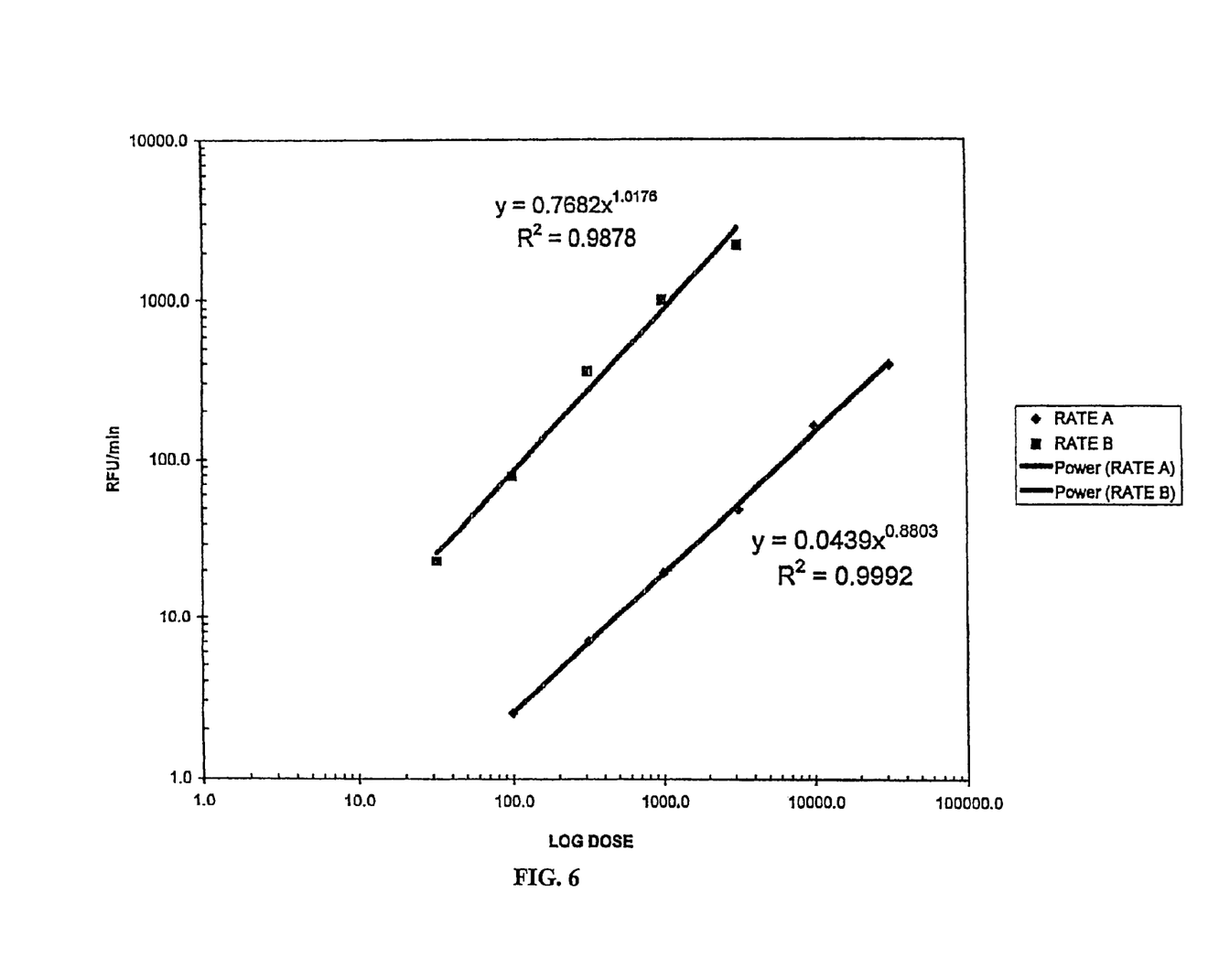
FIG. 6 provides the linear portion (see FIGS. 4 and 5) of the Rate A (--◆--) and Rate B (--■--) curves of amplification of HIV nucleic acids using LAR buffer stored at 37° C. for 69 days.

Half log dilutions of a $1^{e6}$ RNA copies/mL stock were prepared to use as standards. After target capture, the standards were amplified using LAR buffer that had been stored in VIDAS Probe strips at 37° C. for 69 days. The LAR buffer was transferred to fresh strips prior to TMA amplification. Curve results are shown in FIGS. 4-6.

Example 4

Interpretation of the Buffer Heating Results

The increased performance is likely due to improved amplification rather than detection. This is because Vidas Probe is an endpoint assay, and therefore all other amplification components except the specific amplicon are removed before detection. The improved amplification is likely due to increased total amplicon yield, and/or improved specificity. The observation above that the alteration persists after return to 4° C. (FIG. 3) suggested a chemical change has taken place. This could include the appearance of stimulatory compounds or disappearance of inhibitory compounds. This was investigated as described below.

Example 5

HPLC Analysis of Heated Amplification Mixes

The nature of the change in the buffers was investigated with HPLC

A. The 37° C.-treated HIV amplification buffer (LAR; similar but not identical to RAR) was tested to determine what chemical changes might explain that increased amplification (see FIGS. 4-6). A set of eight nucleotide monophosphate (NMPs, dNMPs) as well as eight nucleotide diphosphate standards (NDPs, dNDPs) were prepared by dissolving approximately 2 mg samples of each of them in 4 mL of 10 mM sodium phosphate buffer. For quantitation of these nucleotide samples by UV absorption spectra, each of these stocks were further diluted (1:20) and 100 microliter samples of the diluted solution was used for analysis by the program that examined the individual absorbency readings at 260 nm. Based on the absorbance readings and dilution factor, an average number of OD (absorbance units) present in the individual nucleotide samples was determined. For analysis on HPLC, approximately 300 microliter samples of all the nucleotide sets containing 0.2 OD were used for each run. Samples of HIV LAR 37° C. and HIV LAR 4° C. were used as they were received (1:500 dilution from the original stock). All of these samples were analyzed on the HPLC ion exchange column using 24 nM NaOH buffer and 375 mM perchlorate, 24 mM NaOH buffer to acquire a unique reference profile for each sample based on retention time.

In examining the resulting HPLC profile, several unknown peaks, four of them with less than four minutes retention time and two others at retention times of approximately 9.3 and 10.6 minutes appeared in addition to the eight peaks expected and representative of the NTPs present in the HIV LAR mixture. Upon closer examination, a third unknown peak was visible at a retention time of approximately 6.9 minutes. It was observed that the unknown peaks at 9.3 minutes and 10.6 minutes in the HIV 37° C. sample closely resembled those times obtained for dGDP and GDP, and it was also observed that a peak occurring at a retention time of approximately 6.9 minutes seemed to parallel the profile obtained for TDP.

In order to quantify these results, co-injections of the HIV 37° C. sample with dGDP, GDP, TDP, and UDP were performed. By looking at the areas obtained for the unknown peaks prior to injecting a nucleotide sample, it is possible to formulate a general idea of what the expected areas of the peaks should be and then compare the known peak areas to those obtained after injection. For example, the peak area of the unknown in the HIV 37° C. mix at a retention time of 9.3 was approximately 220,000. However, after injecting 2 microliters of dGDP into 300 microliters of the HIV 37° C. mix, the peak area at the position of the same unknown (approximately 8.95 min. for the particular run) quadrupled to about 800,000, proving that the identity of the unknown was in fact dGDP. Again, this method led to better identification of the other unknown peaks present in the HIV 37° C. run. The area of the unknown peak at 10.6 minutes was about 270,000 before co-injecting 2 microliters of rGDP, whereas the area increased to almost 600,000 after adding the rGDP. Also, the area of the unknown peak at approximately 6.9 minutes doubled from about 105,000 to 280,923 after injecting 1 microliter of TDP to the HIV LAR 37° C. sample. Thus, it is concluded that the identities of the three unknown peaks at 6.9, 9.4 and 10.6 minutes in the HIV LAR 37° C. sample are dGDP, RGDP and TDP. Additionally, it was noted that the breakdown product for CTP, dCTP, ATP, dATP, the diphosphate intermediates, should have short retention times and may correspond to those four peaks with retention times of less than 4 minutes.

Overall, the most notable change detected was that the peaks identifying nucleotide diphosphates (ATP, GTP, CTP, UTP, dATP, dGTP, dCTP, TTP) decreased and were accompanied by the appearance of peaks identified as nucleotide diphosphates. The average level of NTP loss was ~32.5% (see Table 4) It can be concluded that a temperature of 37° C., NTPs, and dNTPs present in the HIV LAR mixture will degrade to their diphosphate forms and some of them (dGDP, GDP, TDP) separate out as distinctive peaks.

TABLE 4

| QHIV Data | | | |
|---|---|---|---|
| NTP | mM 37° C. | mM 4° C. | % |
| dCTP | 2.6 | 4.0 | 65% |
| CTP | 2.8 | 4.3 | 65% |
| dATP | 2.2 | 3.6 | 61% |
| ATP | 3.9 | 4.2 | 93% |
| TTP | 2.6 | 3.8 | 68% |
| UTP | 2.9 | 4.4 | 66% |
| dGTP | 2.2 | 3.6 | 61% |
| GTP | 2.7 | 4.4 | 61% |

B. Analysis of HCV RAR buffer treated at 55° C. and 65° C. (the same samples that showed improved performance in FIG. 2) all revealed significant conversion of NTPs to NDPs (see Table 5). For the three NDP products that were identifiable in clearly resolved peaks (ADP, GDP, dGDP), the vast majority of NTPs were converted to NDPs after 6 days at 65° C. A similar rate of loss for the other NTPs suggests that the effect occurred for all of the NTPs.

TABLE 5

| HPLC analysis of heat treated RAR (HCV) | | | | | | | | | |
|---|---|---|---|---|---|---|---|---|---|
| A. Nucleotide Diphosphate Concentrations (mM) | | | | | | | | | |
| TEMP | DAY | d-CDP | CDP | d-ADP | ADP | TDP | UDP | d-GDP | GDP |
| 55° C. | 1 | | | | 0.58 | | | 0.15 | 0.99 |
|  | 2 | | | | 0.57 | | | 0.15 | 0.98 |
|  | 3 | | | | 1.39 | | | 0.33 | 2.16 |
|  | 4 | | | | | | | | |
|  | 5 | | | | 2.01 | | | 0.27 | 2.82 |
| 65° C. | 1 | | | | 1.24 | | | 0.31 | 2.01 |
|  | 2 | | | | 2.12 | | | 0.52 | 3.54 |
|  | 3 | | | | 2.64 | | | 0.64 | 4.32 |

TABLE 5-continued

HPLC analysis of heat treated RAR (HCV)

| | | | | |
|---|---|---|---|---|
| 4 | | 2.81 | 0.67 | 4.53 |
| 5 | | 2.83 | 0.67 | 4.53 |

B. Nucleotide Triphosphate Concentrations (mM)

| TEMP | DAY | d-CTP | CTP | d-ATP | ATP | TTP | UTP | d-GTP | GTP |
|---|---|---|---|---|---|---|---|---|---|
| 55° C. | 0 | 0.92 | 3.05 | 1.06 | 3.89 | 0.99 | 1.98 | 0.95 | 6.42 |
| | 1 | 0.74 | 2.42 | 0.84 | 3.27 | 0.79 | 1.58 | 0.74 | 5.03 |
| | 2 | 0.72 | 2.40 | 0.82 | 3.22 | 0.79 | 1.57 | 0.74 | 5.02 |
| | 3 | 0.54 | 1.75 | 0.59 | 2.52 | 0.58 | 1.17 | 0.50 | 3.39 |
| | 4 | | | | | | | | |
| | 5 | 0.41 | 1.32 | 0.44 | 2.13 | 0.45 | 0.90 | 0.40 | 2.67 |
| 65° C. | 0 | 0.92 | 3.05 | 1.06 | 3.89 | 0.99 | 1.98 | 0.95 | 6.42 |
| | 1 | 0.57 | 1.85 | 0.63 | 2.62 | 0.61 | 1.22 | 0.55 | 3.70 |
| | 2 | 0.35 | 1.12 | 0.37 | 1.91 | 0.38 | 0.76 | 0.34 | 2.28 |
| | 3 | 0.21 | 0.65 | 0.22 | 1.45 | 0.22 | 0.46 | 0.19 | 1.30 |
| | 4 | 0.12 | 0.36 | 0.12 | 0.27 | 0.12 | 0.27 | 0.10 | 0.68 |
| | 5 | 0.6 | 0.19 | 0.07 | 0.28 | 0.06 | 0.16 | 0.06 | 0.38 |

Example 6

Modified RAR Formulations to Mimic Heat-induced Alteration

Since conversion of NTPs to NDPs appeared to be the most likely cause of the heat-induced effect, performance of an RAR buffer was examined in which, in the buffer, (1) NTPs were partially removed and replaced by NDP addition, (2) NTPs were partially removed, but not replaced by NDPs, and (3) NTPs were not removed but NDPs were added. Target was HCV in vitro transcript as in Example 1.

Figure 7A:
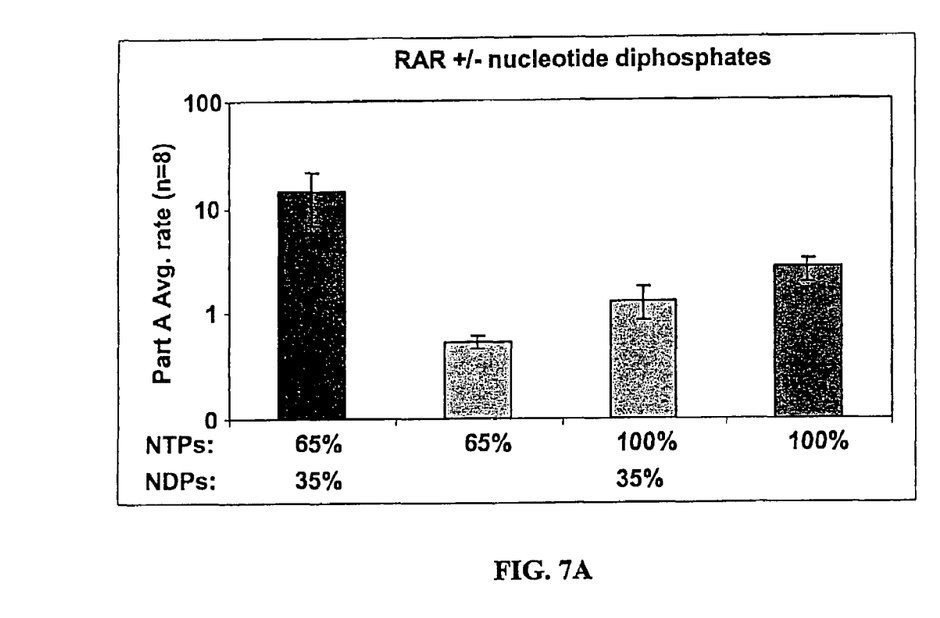
FIG. 7A shows the results of HCV amplification with RAR buffer having partial replacement of NTPs with NDPs, showing that such replacement increases rates. Specifically shown are results wherein 35% of standard amount of NTP (see Table 2) is replaced with NDP; wherein only 65% of standard amount of NTP is used (with no NDPs); wherein 100% of the standard amounts of NTPs are used and additionally an amount equivalent to 35% of standard amount (of NTP) of NDP is added; and wherein 100% of standard amount of NTP is used and no additional nucleotides in the form of NDP are added.
Figure 7B:
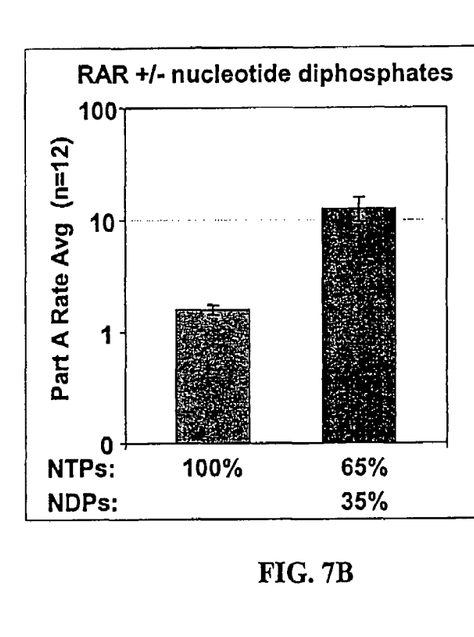
FIG. 7B shows a repeat experiment with the 65%/35% replacement. Data corresponds with Tables 6A and 6B herein.

We determined that replacement of 35% of the nucleotide triphosphates by nucleotide diphosphates (obtained from Sigma) resulted in a significant (>8-fold) enhancement in amplification (see FIG. 7A with Table 6A and FIG. 7B with Table 6B). In contrast, addition of diphosphates without corresponding subtraction of triphosphates (i.e., resulting in a 35% increase in nucleotides) did not increase amplification (FIG. 7 and Tables 6A and B). Similarly, subtraction of nucleotide triphosphates (i.e., resulting in a 35% reduction in nucleotides) did not increase amplification (FIG. 7 and Tables 6A and B). Thus, the partial replacement of triphosphates by diphosphates appears to be a critical component.

Note that the ~40-fold improvement resulting from the RAR buffer heat treatments (FIG. 1, FIG. 2) is higher than that observed in the NTP/NDP replacement experiment shown in FIG. 7 and Tables 6A and B. It is likely that further optimization of nucleotide triphosphate/diphosphate ratios would lead to amplification increases even greater than the 8-fold observed, perhaps similar to or even higher than the heating results. It is possible that NTP/NDP replacement involving only a subset of nucleotides (e.g., replace a fraction of the GTP with GDP, without altering other nucleotides) may improve performance.

TABLE 6A

Trial 1: Results of Partial Replacement of NTPs with NDPs (n = 8) (see also FIG. 7A)

| | NTPs: | | | |
|---|---|---|---|---|
| | 65% | 65% | 100% | 100% |
| | | NDPs: | | |
| | 35% | 0 | 35% | 0 |
| Part A | 14.09 | 0.54 | 1.31 | 2.64 |
| STD | 20.62 | 0.22 | 1.19 | 1.88 |
| % CV | 146% | 41% | 91% | 71% |

TABLE 6B

Trial 2: Results of Partial Replacement of NTPs with NDPs (n = 12) (see also FIG. 7B)

| | NTPs: | |
|---|---|---|
| | 100% | 65% |
| | NDPs: | |
| | 0 | 35% |
| Part A | 1.57 | 12.93 |
| STD | 0.49 | 11.47 |
| % CV | 31% | 89% |

Throughout this application, various publications are referenced. The disclosures of these publications in their entireties are hereby incorporated by reference into this application in order to more fully describe the state of the art to which this invention pertains.

Thus, while there have been described what are presently believed to be the preferred embodiments of the present invention, those skilled in the art will realize that other and further embodiments can be made without departing from the spirit and scope of the invention, and it is intended to include all such further modifications and changes as come within the true scope of the invention.

What is claimed is:

1. A method for performing an amplification reaction that utilizes a buffer that comprises nucleotide triphosphates comprising treating the buffer to substitute a portion of the nucleotide triphosphates with nucleotide diphosphates sufficiently to increase the ratio of nucleotide diphosphates to nucleotide triphosphates in the buffer such that the portion of nucleotide diphosphates is at least 15% prior to adding enzyme and template to the amplification reaction, and performing an amplification reaction utilizing the buffer.

2. The method of claim 1 wherein the treatment comprises heating the buffer to a selected temperature for a selected period of time, the temperature and time each sufficient to increase the ratio of nucleotide diphosphates to nucleotide triphosphates in the buffer such that the portion of nucleotide diphosphates is at least 15%.

3. The method of claim 2, wherein the selected temperature and time period are sufficient to increase the ratio of at least one nucleotide diphosphate to total nucleotide triphosphate to a range from about 35:65 to about 80:20 total nucleotide diphosphate:total nucleotide triphosphate.

4. The method of claim 2, wherein the temperature and time are selected wherein they are inversely related.

5. The method of claim 1, wherein the treatment comprises heating the buffer to a temperature between about 25° C. and 65° C. for a selected period of time.

6. The method of claim 1, wherein the treatment comprises heating the buffer to a temperature between about 37° C. and 65° C. for a selected period of time.

7. The method of claim 1, wherein the treatment comprises heating the buffer to a temperature between about 42° C. and 65° C. for a selected period of time.

8. The method of claim 2, wherein, wherein the period of time is at least 12 hours.

9. The method of claim 2, wherein, wherein the period of time is at least 24 hours.

10. The method of claim 2, wherein, wherein the period of time is at least 14 days.

11. The method of claim 2, wherein, wherein the period of time is at least 21 days.

12. The method of claim 2, wherein, when the temperature of treatment is between about 37° C. and 55° C., the period of time is at least 7 days.

13. The method of claim 2, wherein the when the temperature of treatment is above 55° C., the period of time is up to 4 days.

14. The method of claim 1, wherein the treatment comprises replacing at least 15% of at least one nucleotide triphosphate in the buffer with nucleotide diphosphate.

15. The method of claim 14, wherein the portion of nucleotide triphosphates replaced with nucleotide diphosphates is selected from between about 15% and 80%.

16. A method for performing an amplification reaction that utilizes a buffer that comprises nucleotide triphosphates, comprising reacting a target nucleic acid, an amplification enzyme, and a buffer which has been treated to substitute at least 15% of the nucleotide triphosphates with nucleotide diphosphates sufficiently to increase the ratio of nucleotide diphosphates to nucleotide triphosphates in the buffer, and performing an amplification reaction.

* * * * *